United States Patent [19]
Wentworth et al.

[11] Patent Number: 5,394,092
[45] Date of Patent: Feb. 28, 1995

[54] SYSTEM FOR IDENTIFYING AND QUANTIFYING SELECTED CONSTITUENTS OF GAS SAMPLES USING SELECTIVE PHOTOIONIZATION

[75] Inventors: Wayne E. Wentworth, Pearland; Stanley D. Stearns, Houston, both of Tex.

[73] Assignee: Valco Instruments Co., Inc.

[21] Appl. No.: 176,968

[22] Filed: Jan. 3, 1994

Related U.S. Application Data

[63] Continuation-in-part of Ser. No. 662,149, Feb. 28, 1991, Pat. No. 5,153,519, and a continuation-in-part of Ser. No. 956,632, Oct. 5, 1992, Pat. No. 5,317,271.

[51] Int. Cl.⁶ ............... G01N 27/62; G01N 27/68
[52] U.S. Cl. ....................... 324/464; 324/455; 73/28.02
[58] Field of Search ............ 324/449, 450, 452, 455, 324/464, 123 R, 71.4; 73/23.35, 28.02; 313/231.41, 231.71; 315/111.01, 111.91; 250/379, 385.2; 436/153

[56] References Cited

U.S. PATENT DOCUMENTS

| | | | |
|---|---|---|---|
| 3,540,851 | 11/1970 | Vree et al. | 324/464 X |
| 3,679,973 | 7/1972 | Smith, Jr. et al. | 324/464 X |
| 4,724,394 | 2/1988 | Langer et al. | 324/464 |
| 4,851,683 | 7/1989 | Yang et al. | 250/339 |
| 5,153,519 | 10/1992 | Wentworth et al. | 324/464 |
| 5,317,271 | 5/1994 | Wentworth et al. | 324/464 |

*Primary Examiner*—Gerard R. Strecker
*Assistant Examiner*—Diep Do
*Attorney, Agent, or Firm*—Gunn & Kuffner

[57] ABSTRACT

A spark detection apparatus is set forth and incorporates a closed chamber for receiving a carrier gas flowing therethrough between inlets and outlets, and the carrier gas is exposed to a pair of electrodes forming a spark across the chamber and through the carrier gas. One component of the carrier gas is argon. The sample to be analyzed is injected into the carrier gas. One reaction involves the formation of metastable argon which upon decay serves as a source of ionizing radiation which reacts with sample compounds producing detectable events. These events are used to identify and quantify unknown compounds contained in the sample. The methods and apparatus are especially useful in measuring pollutant compounds in atmospheric samples since the ionizing radiation emitted from the decay of metastable argon is below the ionization potential of the major constituents of air. This greatly enhances the signal-to-noise ratio for detecting impurity compounds when the detection system is used to monitor air quality. Air is not energized.

28 Claims, 1 Drawing Sheet

SYSTEM FOR IDENTIFYING AND QUANTIFYING SELECTED CONSTITUENTS OF GAS SAMPLES USING SELECTIVE PHOTOIONIZATION

This disclosure is a continuation-in-part of application Ser. No. 662,149, filed Feb. 28, 1991, now Pat. No. 5,153,519, and also Ser. No. 07/956,632, filed Oct. 5, 1992, now U.S. Pat. No. 5,317,271.

BACKGROUND OF THE DISCLOSURE

The present disclosure involves the quantitative analysis of gases for compounds of interest and is an extension of the apparatus and methods taught in U.S. Pat. No. 5,153,519. More specifically, the invention is directed, although not limited, to the classification and quantification of impurities in air.

The referenced patent discloses the creation of several charged species by a pulsed direct current (DC) spark discharge acting on a carrier gas containing other compounds to be identified and quantified, where the carrier gas is typically helium. The charged species are used to classify and/or quantify the unknown compounds in the carrier. This detector is connected with upstream or downstream devices such as a sample source, gas chromatograph (GC) column, spectrum analyzer or the like. A sample to be analyzed is loaded for flow along with the carrier gas into a system chamber. While the sample passes through the detection device, a pulsed, high voltage DC spark discharges to form selected charged or energized species within the gas. The spark discharge simultaneously initiates several types of detection systems. For instance, the very short DC spark creates a readily available thermalized electron flux which can be used in a detection system. In an alternate mode of operation, the spark creates a more slowly diffused flux of metastable helium atoms which drift toward selected electrodes within the detector at a controlled rate. The helium atoms will react with molecules of the sample to surrender the excess energy from the excited state to cause sample molecule ionization which, as a secondary and delayed reaction, can be measured by a detection system. Another aspect involves photoionization of gas into positive and negative charged particles normally recombining at high speed. If a select sweep pulse voltage is applied, the recombination is prevented to furnish a signal indicative of the unknown compounds within the gas mixture. Identification and quantification of compounds of interest can, to some extent, be controlled by varying the timing of the spark, the electrode geometry, the voltages of the detector segments, and the modes of interactions observed within the plasma. A complete discussion of the apparatus and basic principles of the measurements are disclosed in detail in U.S. Pat. No. 5,153,519 and are incorporated herewithin by reference.

SUMMARY OF THE INVENTION

The monitoring of trace compounds such as pollutants in the atmosphere is of great environmental and economic importance. As an example, it is not possible to use the referenced high voltage spark excitation and ionization detection to selectively ionize pollutant compounds in an atmospheric sample without ionizing the major constituents of air such as nitrogen, oxygen, water and carbon dioxide. Spectroscopic techniques can be used to analyze atomic or molecular emission lines; however, emissions from trace compounds are often masked by emissions from the major constituents of air. It is, therefore, highly desirable to ionize only trace pollutants and not ionize the major constituents of air. In addition and extending the concept to air, other carrier gas systems can be envisioned for use with this test system.

Selective ionization of only trace compounds in an atmospheric sample is accomplished by using a mixture of argon and helium as a carrier gas in the high voltage spark excitation and ionization detector. The percent concentration of argon in helium is somewhat less than 1.0% and preferably approximately 0.3%. The spark discharge is used to excite the helium-argon gas mixture which results in the emission of photons arising from the well known resonance lines of argon at 104.8 and 106.6 nm. An important aspect of the argon emission is that it is used to ionize only impurities in air. The argon resonance lines have energies of 11.62 and 11.83 eV, which are less than the ionization potentials of common and major components of air such as nitrogen at 15.6 eV, oxygen at 12.08 eV, water at 12.6 eV, and carbon dioxide at 11.8 eV. Argon emission therefore avoids ionizing the major constituents of air while ionizing impurities with ionization potentials less than 11.8 eV. The pulsed discharge source is used with a mixture of helium and argon as a carrier gas as a selective photoionization source. This can be applied in a photoionization gas chromatographic detector where the argon-helium gas mixture is passed through the discharge electrodes and the argon radiation passes through the referenced ionization detector so that the argon radiation is absorbed by the analytes reacts with the analytes, and so that those components with ionization potentials less than 11.8 eV are then ionized and detected by the electron current generated on the collecting electrode.

Argon emission can also be used effectively in selective ionization of components being analyzed by ion mobility spectrometry or atmospheric pressure ionization mass spectrometry. In these applications, the positive ions arising from selective photoionization are detected in addition to the collection of electrons. Again, the selectivity of argon radiation is especially important in the ionization of impurities in air.

Argon emission induced by a high voltage spark is ideally suited for use in an air monitoring device for the detection of pollutants originating from chemical spills or leaks. The principals of detection are the same as those summarized above and further disclosed, in part, in the referenced parent application and U.S. patent. The airborne pollutants are ionized by the argon resonance emission, while the major constituents of air are not ionized since their ionization potentials are above that of the 11.62 and 11.83 eV emissions of argon. Prior art detection has utilized a source external to the gas sample as a source of ionizing radiation for such measurements. Current methods utilize a photoionization lamp containing a window with transparency above approximately 118 nm so that compounds with ionization potentials above approximately 10.5 eV are not ionized. In the current invention, the argon ionization source is not external to the sample but, in fact, is created by direct exposure of the sample to the argon photoemission. The argon, after excitation, emits photons at 11.62 and 11.83 eV which are absorbed by the sample. The disclosed invention therefore increases the range of sample ionization from approximately 10.5 eV (the transparency limit of the photoionization lamp) to approximately 11.8 eV (the higher energy argon emission line). This, in turn, allows the air sample to be analyzed for an expanded number of pollutants having ionization potentials within the range of approximately 10.5 to 11.8 eV, while excluding ionization of major components of air.

BRIEF DESCRIPTION OF THE DRAWINGS

So that the manner in which the above recited features, advantages and objectives of the present invention are attained and can be understood in detail, more particular description of the invention, briefly summarized above, may be had by reference to the embodiments thereof which are illustrated in the appended drawings. It is to be noted, however, that the appended drawings illustrate only typical embodiments of the invention and are therefore not to be considered limiting of its scope, for the invention may admit to other equally effective embodiments.

DETAILED DESCRIPTION OF THE PREFERRED EMBODIMENT

The present disclosure is directed to an ionization detector system connected upstream or downstream with existing equipment. The cooperative equipment constitutes one context for ease of explanation. This detector system is devoid of radioactive sources and hence can be used where radioactive materials are limited. Heretofore, it has been common to operate electron capture devices with radioactive material such as a source of ionizing radiation, the most common being tritium and nickel-63.

Figure 1:
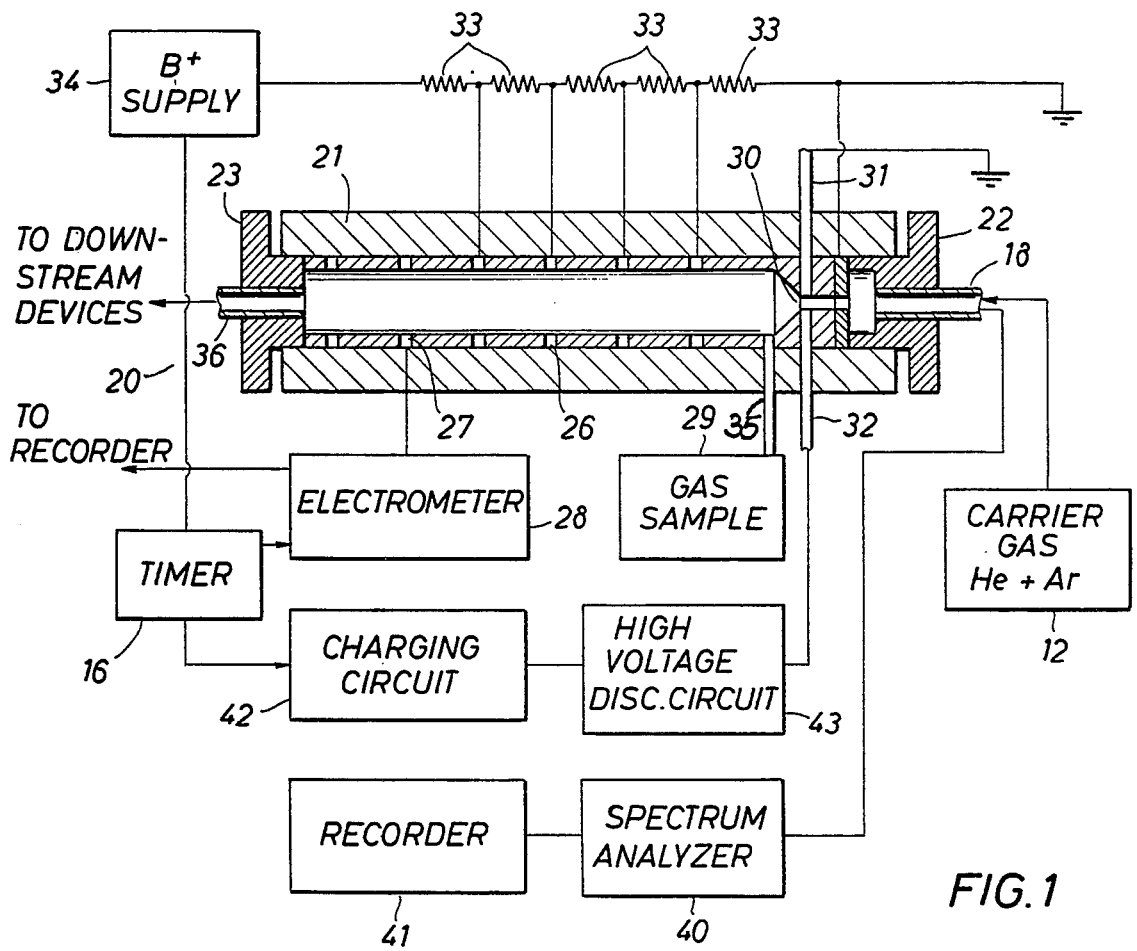
FIG. 1 is a schematic block diagram of the detector showing a pair of fixed electrodes in a spark gap for pulsed DC discharge in a flowing stream to form charged particles and metastable atoms, preferably argon while a sample to be analyzed is injected into the detector downstream from the spark gap.

Referring to FIG. 1, the numeral 20 identifies the detector system of the present invention. Operation will be described in the fashion of a flow chart.

The present detector system utilizes a carrier gas source 12 connected to the detector with an input valve (not shown). The source 12 provides a steady flow of carrier gas into and through the detector at a controlled flow rate and pressure. The sample to be analyzed is injected into the carrier gas flowing within the detector as will be discussed later. Representative sample compounds may include various and sundry organic compounds which will, for purposes of illustration, be denoted in very general terms as the compound AB. The concentration of compound AB can, of course, vary the sample. The detector 20 is able to identify and quantify the concentration of the compound AB as few as parts per million, parts per billion or even smaller concentrations. The carrier gas is helium containing a relatively small concentration of argon, preferably of the order of 0.3%. The carrier gas is directed to the inlet opening 18 of the detector 20. This detector 20 includes a closed elongated tube 21 which has an end cap 22 opposite a similar end cap 23, both being provided with ports for gas flow through the detector. The central tube 21 is hollow and has a uniform diameter throughout the length except at the spark electrodes as will be mentioned.

The detector 20 is formed of an insulating material such as glass or the like. Carrier gas from the source 12 enters the detector 20 through an inlet opening 18. The flow of carrier gas then flows through a spark gap 30 and then through the elongate chamber. Sample gas from a source 29 is injected into the tube 21 of the detector 20 through a port 35. The sample gas can be samples of air, elute from a gas chromatograph (GC) column, or the like. Exposed metal rings are spaced along the tube 21. One of the rings is more remote while other rings are serially closer. The rings are arranged serially downstream from the inlet end 18. There are several intermediate rings 26 which are tied to various resistors 33 for voltage drops as described or detailed in previously referenced U.S. Pat. No. 5,153,519. There is also a ring 27 which is connected to an electrometer 28. The electrometer can be connected to electrodes elsewhere along the length of tube 21. It is connected to a selected or particular terminal which is exposed to charged particle population within the tube 21 to detect current flow resulting from charged particle migration.

The numeral 30 identifies a spark gap which is defined by two round and equal diameter rods. They have a finite width which measures a fraction of a millimeter up to about two millimeters. The tips are cut flush with the inner passage to form opposing, parallel faces. The two tips are aligned with one another such that they are precisely diametrically opposite each other within the passage and thus define the spark gap 30. The spark gap 30 is downstream in the flow of carrier gas which is input into the chamber at inlet opening 18. They are supported by the surrounding structure of non-conducting material such as glass, plastic, ceramic or the like. All flowing carrier gas must pass between the two spaced tips. This passage is ideally small in diameter, perhaps having a diameter of about one millimeter, and it can be less. The two electrodes are preferably spaced from one to another by something between 0.5 and 1.5 millimeters. They can be slightly farther apart if desired.

The two electrodes are identified by the numerals 31 and 32 with the electrode 31 grounded. The electrode 32 is provided with a high voltage pulse as described in previously referenced U.S. Pat. No. 5,153,519. A very short pulse is preferred. The caps 22 and 23 at the two ends of the structure seal against the intrusion of external air so that only the gases flowing through the system are the carrier gas which preferably is a mixture of helium and argon and the sample compound AB. Argon within the flowing stream of carrier gas interacts with the spark as the carrier gas flows through the spark discharge. The sample gas containing compound AB is injected into the carrier gas at port 35 downstream from spark gap 30. The photons given up by the argon can react over a significant distance. Therefore, the added sample flow can mix poorly or mix well in the tube 21; no special effort is normally required to obtain adequate exposure to the sample for argon emission.

The several electrodes 26 are connected to a voltage ladder which is made up of several series connected resistors 33. B+ voltage is provided for the system by B+ supply 34. As is well known a negative voltage at the B+ supply is also permitted. Thus, the electrodes have the requisite voltage (positive or negative) to attract the desired charged particles. B+ voltage is pulsed and is controlled by a timer 16. The voltage can be positive or negative and is proportioned by the resistors 33. The flowing gases are directed through the spark gap 30. Sample gas containing the compound AB is injected through port 35 at which point the sample and makeup gases commingle. The mixture subsequently exits the chamber tube 21 through the exit port 36. The port 36 is aligned with the port 18 at the opposite end. The port 18 serves as an observation port to enable observation of the gap during the spark. This enables photons of light emitted at the spark gap 30 to impinge on an external spectrum analyzer 40 which is positioned opposite the outlet opening 18. In turn, the analyzer connects with a recorder 41 for recording the data as a function of time. The system also includes a charging circuit 42 which connects with a high voltage discharge circuit 43 to provide a timed pulse for firing.

Figure 2:
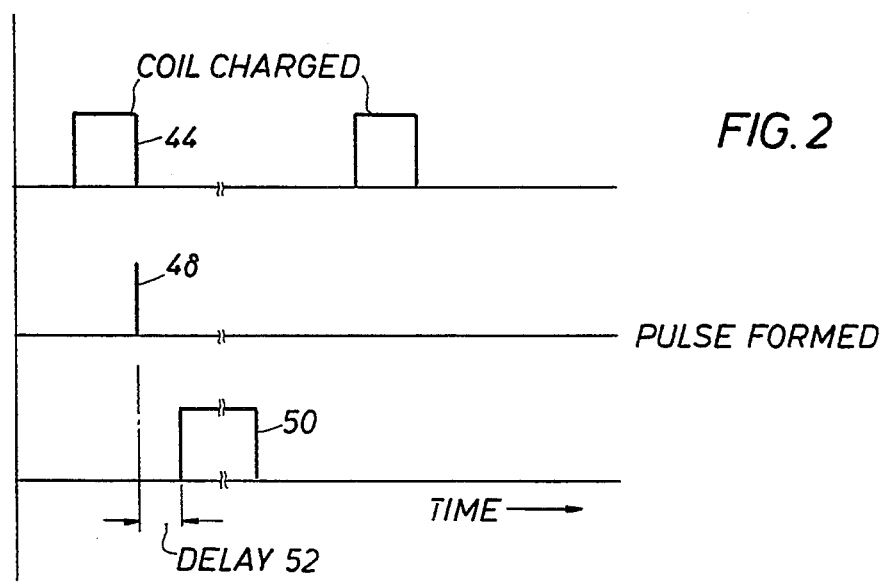
FIG. 2 is a timing chart showing the timed relationship of operations of circuitry shown in FIG. 1 of the drawings.

FIG. 2 of the drawings depicts several curves which are shown as a function of time. The top curve shows the charging current in the pulse 44 which forms the necessary charge for the operation of the high voltage discharge circuit 43. That circuit forms an output 48 which is a discharge pulse of relatively short duration in time. There is a detection interval which is delayed by a specified time 52, and then a detection pulse is formed at 50.

Helium and argon (defining the carrier gas) mixture flows into the detector 20 through inlet port 18 and ultimately into the spark gap 30 where ions and atoms in the excited state are formed. In particular, the argon component of the carrier gas is energized and raised to an excited state. The excited argon passes from the vicinity of the spark gap 30 into the cavity portion 21 of the detector 20. Argon in the excited state emits photons associated with the well known resonance lines of argon at 104.8 and 106.6 nm with corresponding energies of 11.62 and 11.83 eV, respectively. By mixing argon with the primary makeup gas helium and exciting the carrier gas mixture at the spark gap 30, excited argon (Ar*) is created along with other components. These other components are detailed in previously referenced U.S. Pat. No. 5,153,519. As the carrier gas containing Ar* passes from the spark gap 30, sample gas containing the compound AB is commingled with the carrier gas by injection through the port 35. As a result of this process, the source of ionizing radiation, namely Ar*, is in the closest proximity to the sample to be ionized and quantified, namely compound AB. Possible ionization type reactions that can be induced by the Ar* source are:

  (1)

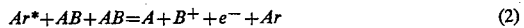  (2)

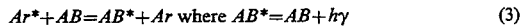  (3)

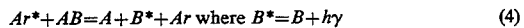  (4)

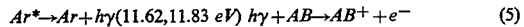  (5)

where $e^-$ denotes a free electron, * denotes an excited state, and $h\gamma$ denotes spectral emission. Equations (3) and (4) describe reactions which form specific and characteristic emission spectra, thereby providing a characteristic signal which enables identification and quantification of the unknown sample compound AB. Spectral analysis is performed with the spectrum analyzer 40. Unknown compounds are identified and their concentrations are determined. More specifically, different species of excited compounds, designated as $AB^*_i$ using the nomenclature of the previous equations, emit photons of characteristic energy upon decay to the ground state. A measure of the energies of these photon emissions using spectrum analyzer 40 provides a means of identifying specific "unknown" compounds $AB_i$. Emission energies for most compounds are known. If these characteristic emissions are not known for a given compound, the apparatus can be calibrated for this compound by measuring emissions using a calibration sample containing only the unknown compound. The concentrations of the unknown compounds are determined from the measured intensity of the characteristic emissions. The calibration relationships between measured intensity and concentration is determined by measuring emission intensity as a function of known concentrations of compounds in calibration samples. Equations (1) and (2) describe reactions which produce free electrons. Ions are also formed. For a given voltage supplied by power supply 34, the mobility of ions formed are a function of the parent compound. Using the reaction depicted in Equation (1) as an example, and using previously defined nomenclature, an ion $AB^+_1$ may be more mobile than an ion $AB^+_2$. If the sample gas contained both compounds $AB_1$ and $AB_2$, currents recorded by electrometer would show two maxima as a function of time following the spark discharge, where the earlier maximum would result from the flow of ions $AB^+_1$ and the later maximum would result from the flow of ions $AB^+_2$. Relationships between ion mobility and the identity of the corresponding parent ions can be determined by operating the apparatus using calibration sample gases with known compounds. The type of compound can, therefore, be determined by a measure of ionic mobility. The corresponding concentration is determined by the magnitude of the current maxima, again using previously mentioned calibration procedures with known calibration gases. An increase in current maxima indicates a corresponding increase in concentration of the corresponding compound. Delay times 52 can be adjusted to bias out current maxima from compounds not to be measured. Other parameters such as the applied voltage, the duration 48 of the spark, and even the flow rate of carrier gas can be adjusted to maximize the accuracy and precision of measurements of compounds of interest while minimizing contributions from other compounds which might be within the sample gas.

Ar* emits radiation at 11.62 and 11.83 eV. This radiation will not ionize any compound AB with an ionization potential above 11.83 eV. The major components of air are nitrogen with an ionization potential of 15.6 eV, oxygen with an ionization potential of 12.08 eV, water with an ionization potential of 12.6 eV and carbon dioxide with an ionization potential of 13.8 eV. If, therefore, air is the sample gas, the major constituents of air will not be ionized by the Ar* source, but impurities in the air sample such as pollutants with ionization potentials below 11.83 eV will be ionized. The pulsed discharge source can therefore be used with a makeup gas mixture of predominately helium and a relatively small percentage of argon as a selective photoionization source. This can be applied in a photoionization GC detector where the discharge serves as a sample source and the argon radiation passes through the previously described ionization detector until it is absorbed by the analytes coming from the GC column. At this point within chamber 21, the radiation from argon is absorbed by the analyte, and those components with ionization potentials less than approximately 11.8 eV will become ionized and detected by the electron current generated on the collecting electrode 27 and recorded by the electrometer 28.

The argon emission can be used effectively in selective ionization of components being analyzed by ion mobility spectrometry or atmospheric pressure ionization mass spectrometry. In these applications the ions arising from the selective photoionization are detected in addition to the collection of electrons using methods described in detail in referenced U.S. Pat. No. 5,153,519. Again, the use of this radiation is especially important in the ionization of impurities such as pollutants in air.

Argon emission can also be used in air monitoring devices for the detection of pollutants originating from chemical spills or leaks. The principles of the detector are the same as disclosed previously, where the pollutants are selectively photoionized by the argon resonance emission while the major constituents of air remain un-ionized thereby greatly increasing the sensitivity of the measurement by increasing the signal-to-noise ratio. Because the ionizing radiation Ar* is mixed within the chamber 21 with the sample being analyzed, a window is not needed in the wall of chamber 21 through which to inject ionizing radiation from an external source. Since a window is not used or needed, compounds with higher ionization potential can be detected than possible with prior art systems. In the prior art, photoionization arises from photons from a photoionization lamp containing a window with transparency above approximately 118 nm so that compounds above approximately 10.5 eV are not ionized and are therefore not detected and analyzed. The current invention now allows the analysis of additional impurity compounds with ionization potentials up to between approximately 10.5 eV and approximately 11.8 eV.

In summary, the preferred embodiment of the disclosure is directed toward, although not limited to, the quantitative analysis of samples of air for trace constituents such as pollutants. The major constituents of air, in approximate percentage by volume, are nitrogen at 78%, oxygen at 21%, water ranging from a trace to 2% or more, and carbon dioxide at 0.04%. The detection system as disclosed does not ionize and therefore does not directly detect these major constituents. Only trace constituents such as organic pollutants with ionization below the major air constituents are ionized and detected. Interferences from the major constituents are eliminated thereby greatly increasing the sensitivity, precision and accuracy of the measurement for the trace constituents of interest.

While the foregoing disclosure is directed to the preferred embodiments of the present invention, other and further embodiments of the invention may be devised without departing from the basic scope thereof, and the scope thereof is determined by the claims which follow.

What is claimed is:

1. A method for analyzing a sample compound in a carrier gas comprising the steps of:
    (a) through a first inlet, flowing said carrier gas through a chamber for exposure to pulsed DC current across the chamber;
    (b) energizing at least one component of said carrier gas to an excited state as a result to exposure to said pulsed DC current;
    (c) flowing a gaseous sample compound into said chamber through a second inlet downstream from said first inlet and downstream from said pulsed DC current thereby commingling said gaseous sample compound with said carrier gas;
    (d) forming charged particles in the gaseous sample as a result of ionizing radiation emitted in the decay of said excited component of said carrier gas wherein the charged particles are formed from said gaseous sample;
    (e) measuring said charged particles wherein said measurement occurs in timed relationship with respect to said pulsed DC current; and
    (f) selectively determining types and concentrations of compounds contained in said gaseous sample by utilizing said measurements.

2. The method of claim 1 wherein said carrier gas comprises argon.

3. The method of claim 2 wherein helium is the larger component and argon is the smaller component of said carrier gas.

4. The method of claim 1 wherein said ionizing radiation is below the threshold energy level of air.

5. A method of analyzing a sample compound comprising the steps of:
    (a) flowing a carrier gas through a chamber for exposure to DC current thereby energizing at least one component of said carrier gas to an excited state as a result of exposure to said DC current;
    (b) commingling a gaseous sample with said carrier gas within a chamber wherein said carrier gas comprises at least one component in an excited state;
    (c) forming one or more excited compounds in said gaseous sample resulting from photon emission in the decay of at least one excited component of said carrier gas wherein the emissions involve an energy exchange up to about 11.8 eV; and
    (d) determining the type and concentration of one or more compounds in said gaseous sample by measuring photon emission from the decay of said excited compounds in said gaseous sample.

6. The method of claim 5 wherein one component of said carder gas is argon.

7. The method of claim 6 wherein said observation is made during DC current flow.

8. The method of claim 6 wherein said observation is made in a region of said chamber not including said current flow.

9. The method of claim 8 wherein the carrier gas comprises helium and argon, and the observed optical emissions are induced by ionizing radiation emitted by argon which is energized to a metastable state.

10. A gas detector for identification and quantification of sample compounds, comprising:
    (a) an elongated chamber having a first chamber inlet at one end an outlet at the other end, and a gas flow path between said first inlet and outlet ends;
    (b) two electrodes spaced apart and located to produce short, repeated, high voltage, pulsed DC current within said chamber across said gas flow path and wherein spark duration minimizes electrode erosion and permits observation of phenomena occurring at and between said DC current at and remote from said electrode location;
    (c) means for introducing a carrier gas into said chamber through said first chamber inlet and flowing said carrier gas in said gas flow path;
    (d) means for introducing a sample gas into said chamber through a second inlet which is located downstream from said first chamber inlet and downstream from said two spaced electrodes, and flowing said sample gas in said gas flow path; and (e) wherein ions are produced by said spark or by metastable species of said carrier gas.

11. The apparatus of claim 10 wherein a potential gradient is created between said spark electrodes and a collector electrode in said chamber for the measurement of ionization.

12. The apparatus of claim 11 wherein a series of electrodes provides a focusing electrical gradient to control and measure the mobility of ions formed by said spark.

13. A method of selectivity analyzing a sample of air for impurities comprising the steps of:

(a) flowing a carrier gas comprising argon through a chamber for exposure to periodically pulsed DC currents across said chamber;

(b) energizing said argon to an excited metastable state as a result of exposure to said current;

(c) commingling an air sample with said carrier gas within said chamber by inputting said air sample into said chamber downstream from the input of said carrier gas and downstream from said periodically pulsed DC current across said chamber;

(d) forming charged particles as a result of ionizing radiation emitted by the decay of said argon component of said carrier gas in said chamber, and wherein the charged particles are formed by selective ionization of impurities of said air sample based on ionization potentials of said impurities while precluding ionization of major constituents of air; and (e) observing reactions induced by ionizing radiation produced by the decay of said metastable argon with said impurities of said air sample.

14. The method of claim 13 wherein said impurities are identified and quantified by measuring charged particles resulting from the ionization of impurities produced by ionizing radiation emitted by the decay of said metastable argon.

15. The method of claim 13 wherein said impurities are identified and quantified by observing spectral emission of impurities induced by ionizing radiation from the decay of said metastable argon.

16. The method of claim 13 wherein said observations are made during said spark discharge.

17. The method of claim 13 wherein said observations are made remote from said spark gap and at a time following said spark discharge.

18. The method of claim 13 wherein impurities with ionization potentials below approximately 11.8 eV are observed.

19. The method of claim 13 wherein the major constituent of said carrier gas is helium and the second constituent is argon in a concentration of approximately 0.3%.

20. A method of testing an airborne sample comprising the steps of:

(a) providing an airborne sample flowing through a test chamber;

(b) simultaneously providing a carrier gas flowing through said test chamber;

(c) within said test chamber, forming with an electrical current a metastable species in said carrier gas wherein said metastable species is characterized by having a ground energy state and excited state of sufficient time duration to enable an energy transfer from said excited state of said metastable species to said airborne sample by the emission of photons; and (d) wherein the excited state causes an energy transfer to said airborne sample wherein the excitation energy range of said metastable species is selected to preclude energizing the constituents of air.

21. The method of claim 20 wherein air constituents of nitrogen, oxygen, water vapor and carbon dioxide are not energized.

22. A method for analyzing a sample compound in a carrier gas, comprising the steps of:

(a) through a first inlet, flowing said carrier gas through a chamber for exposure to pulsed DC current across said chamber wherein said carrier gas comprises argon;

(b) energizing at least one component of said carrier gas to an excited state as a result of exposure to said pulsed DC current;

(c) flowing a gaseous sample compound into said chamber through a second inlet downstream from said first inlet and also downstream from said pulsed DC current thereby commingling said gaseous sample with said carrier gas;

(d) forming charged particles in the gaseous sample as a result of ionizing radiation emitted in the decay of said excited component of said carrier gas wherein said charged particles are formed from said gaseous sample;

(e) measuring said charging particles wherein said measurement occurs in timed relationship with respect to said pulsed DC current; and (f) selectively determining types and concentrations of compounds contained in said gaseous sample by utilizing said measurements.

23. The method of claim 22 wherein helium is the larger component and argon is the smaller component of said carrier gas.

24. The method of claim 23 wherein said ionizing radiation is below the threshold energy of air.

25. A method for analyzing a sample compound comprising the steps of:

(a) flowing a carrier gas comprising argon through a chamber for exposure to DC current thereby energizing at least one component of said carrier gas to an excited state as a result of exposure to said DC current;

(b) commingling a gaseous sample with said carrier gas within said chamber wherein said carrier gas comprises at least one component in an excited state;

(c) forming one or more excited compounds in said gaseous sample resulting from photon emission in the decay of at least one excited compound of said carrier gas wherein emissions involve energy exchange up to about 11.8 eV; and (d) determining the type and concentration of one or more compounds in said gaseous sample by measuring photon emission from the decay of said excited compounds in said gaseous sample.

26. The method of claim 25 wherein said observation is made during the DC current flow.

27. The method of claim 25 wherein said observation is made in a region of said chamber not including said DC current flow.

28. The method of claim 27 wherein the carrier gas comprises helium and argon, and the observed optical emissions are induced by ionizing radiation emitted by argon as said argon decays from a metastable state.

* * * * *